(12) United States Patent
Fujieda

(10) Patent No.: US 7,840,041 B2  
(45) Date of Patent: Nov. 23, 2010

(54) DEVICE FOR CONVERTING MEDICAL IMAGE DATA

(75) Inventor: Masami Fujieda, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1253 days.

(21) Appl. No.: 11/279,957

(22) Filed: Apr. 17, 2006

(65) Prior Publication Data
US 2006/0239394 A1    Oct. 26, 2006

(30) Foreign Application Priority Data
Apr. 20, 2005    (JP)    ............... 2005-122489

(51) Int. Cl.
*G01N 23/00* (2006.01)

(52) U.S. Cl. .......................... 382/128; 378/1

(58) Field of Classification Search .............. 378/1; 382/128
See application file for complete search history.

(56) References Cited

U.S. PATENT DOCUMENTS

| 5,300,947 | A * | 4/1994 | Katsura et al. | 345/600 |
| 6,832,001 | B1 * | 12/2004 | Kashiwagi | 382/166 |
| 2002/0181660 | A1 * | 12/2002 | Reinstein et al. | 378/205 |
| 2005/0107691 | A1 * | 5/2005 | Zalis | 600/425 |
| 2005/0219241 | A1 * | 10/2005 | Chun | 345/419 |
| 2006/0239524 | A1 * | 10/2006 | Desh et al. | 382/128 |

FOREIGN PATENT DOCUMENTS

| JP | 2005-296333 | 10/2005 |
| KR | 10-2006-0062680 | 6/2006 |

* cited by examiner

*Primary Examiner*—Samir A. Ahmed  
*Assistant Examiner*—John W Lee  
(74) *Attorney, Agent, or Firm*—Oblon, Spivak, McClelland, Maier & Neustadt, L.L.P.

(57) ABSTRACT

A converting device that carries out data conversion on medical image data expressing a state of one pixel of a medical image using effective bits, which are part of a plurality of bits for one pixel and expressing information other than the medical image using redundant bits, which are different part from that of the effective bits, the converting device includes an invalidating unit that invalidates data expressed by the redundant bits.

7 Claims, 8 Drawing Sheets

DEVICE FOR CONVERTING MEDICAL IMAGE DATA

CROSS-REFERENCE TO RELATED APPLICATIONS

This application is based upon and claims the benefit of priority from prior Japanese Patent Application No. 2005-122489, filed Apr. 20, 2005, the entire contents of which are incorporated herein by reference.

BACKGROUND OF THE INVENTION

1. Field of the Invention

The present invention relates to a converting device for medical image data which express the state of one pixel of a medical image by using effective bits, which are part of a plurality of bits for one pixel, and further express data other than those for the medical image by using a part of redundant bits, which are different from the effective bits.

2. Description of the Related Art

Recently, for the medical image data, formats adhered to the standard of, for example, ACR-NEMA (American college of radiology—national electrical manufactures association) V2.0 or DICOM (digital imaging and communications in medicine) are used. In such medical image data, personal data relating to a patient are expressed in the form of tag data, which are separate from actual data. Therefore, with the deletion of the tag data, the personal data can be concealed without making any influence to the actual data.

However, in those medical image data that were formed before the above-described standards were established, personal data were, in many cases, embedded in actual data. For example, of all bits (for example, 12 bits) for one pixel, some (for example, lower 8 bits) of these bits are used for the data of each pixel of a medical image, and the rest (for example, upper 4 bits) of the bits are used for each pixel of a text image that indicates personal data. In the case of such medical image data, the personal data cannot be concealed by deleting the tag data.

BRIEF SUMMARY OF THE INVENTION

Under the above-described circumstances, there has been a demand for a technique of converting data to conceal personal data even in the case of medical image data that express personal data by using some of bits for one pixel.

According to an aspect of the present invention, there is provided a converting device that carries out data conversion on medical image data expressing a state of one pixel of a medical image using effective bits, which are part of a plurality of bits for one pixel and expressing information other than the medical image using redundant bits, which are different part from that of the effective bits, the converting device comprising: an invalidating unit that invalidates data expressed by the redundant bits.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will now be described with reference to accompanying drawings.

Figure 1:
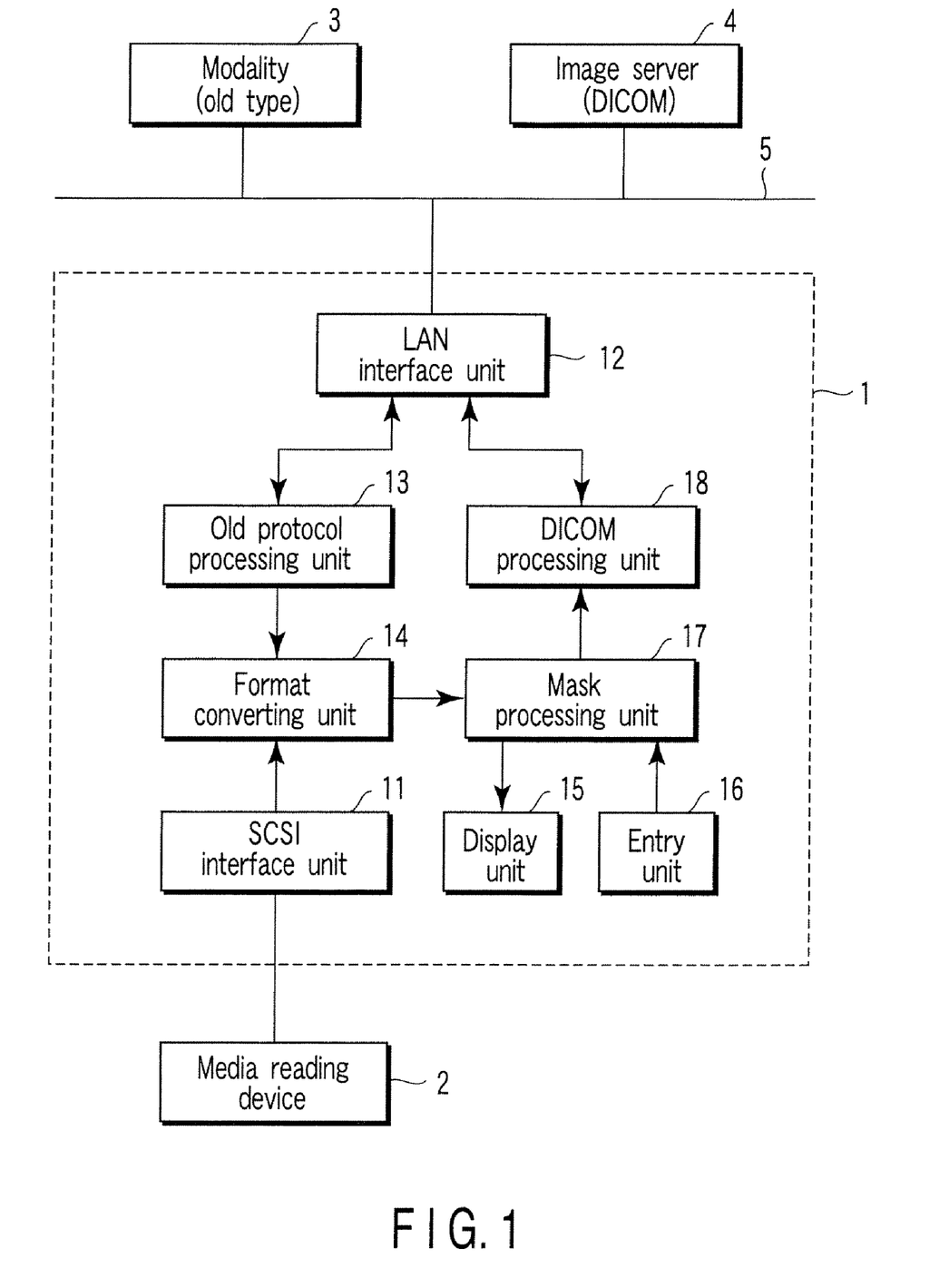
FIG. 1 is a block diagram showing the structure of a converting device according to an embodiment of the present invention.

FIG. 1 is a block diagram showing the structure of a converting device 1 according to the embodiment. The converting device 1 obtains medical image data of an old format from a media reading device 2 or a modality 3. Then, the converting device 1 converts the data into those of a new format that adheres to the DICOM and send the converted data to an image server 4.

The media reading device 2 reads the medical image data of the old format, stored on a recording medium such as an optical disk. The converting device 1 and the media reading device 2 are connected to each other using a SCSI (small computer system interface). Here, it is alternatively possible to use some other interface such as GPIB (general purpose interface bus) in place of SCSI.

The modality 3 is a conventional device used to obtain a medical image of a patient, that is, for example, an X-ray computer tomographic diagnosing device (X-ray CT), magnetic resonance imaging device (MRI), X-ray image diagnosing device or ultrasonic diagnosing device. The modality 3 is of an old type that does not adheres to DICOM, and outputs medical image data of the old format, which express the obtained medical image.

The image server 4 stores medical image data of such formats that adhere to DICOM.

The converting device 1, modality 3 and image server 4 can communicate with each other via a LAN 5.

It should be noted that the old format is different from that of ACR-NEMA V2.0, DICOM, or the like, which expresses additional data as tag data separated from actual data, but it is a format that divides the bits for one pixel into parts to express actual data and additional data, respectively. The actual data are data that express medical images such as tomograms and perspective images. The actual data express the state of each of many pixels that are two or three dimensionally arranged in bits. The additional data are data that express additional information other than medical image. The personal data of a patient are included in the additional data. The format of the additional data may be arbitrary. In the following descriptions, the additional data are those expressing a text image. In other words, the additional data express the state of each of many pixels that constitute a text image expressing additional information in 1 or more bits.

The converting device 1 includes a SCSI interface unit 11, a LAN interface unit 12, an old protocol processing unit 13, a format converting unit 14, a display unit 15, an entry unit 16, a masking unit 17 and a DICOM processing unit 18.

The SCSI interface unit 11 transmits and receives data to and from an external device using SCSI. When the media reading device 2 is to be used, the media reading device 2 is connected to the SCSI interface unit 11. The SCSI interface unit 11 fetches medical image data output from the SCSI interface unit 11. The SCSI interface unit 11 supplies the fetched medical image to the format converting unit 14. The SCSI interface unit 11 can be realized by utilizing, for example, a conventional SCSI interface circuit.

The LAN interface 12 receives data that come in via the LAN 5, and supplies the data to the old protocol processing unit 13 and the DICOM processing unit 18. The LAN interface unit 12 sends out the data output from the data to the old protocol processing unit 13 and the DICOM processing unit 18 to the LAN 5. The LAN interface unit 12 can be realized by utilizing, for example, a conventional LAN interface circuit.

The old protocol processing unit 13 processes a communication protocol utilized by the modality 3 to transfer medical image data, and then fetches the medical image date from the modality 3. The old-protocol processing unit 13 supplies the fetched medical image data to the format converting unit 14.

The format converting unit 14 converts the medical image data supplied from the SCSI interface unit 11 or the old protocol processing unit 13, from the old format to a DICOM format. The format converting unit 14 supplies the converted medical image data to the masking unit 17.

The display unit 15 displays the image expressed by the medical image data at a request from the masking unit 17. The display unit 15 can be realized by utilizing a conventional display device such as a liquid crystal display.

The entry unit 16 is used to enter various types of instructions by the user. The entry unit 16 can be realized by utilizing a conventional entry device such as mouse. The instructions input with the entry unit 16 includes those regarding an object area in which the mask process is to be carried out.

The masking unit 17 carries out a mask process to invalidate the additional data contained in the medical image data, which will be explained later. The masking unit 17 supplies the mask-processed medical image data to the DICOM processing unit 18.

The DICOM processing unit 18 transfers the medical image data supplied from the masking unit 17 to the image server 4 in the protocol adhered to DICOM.

The old protocol processing unit 13, the format converting unit 14, the mask process unit 17 and the DICOM processing unit 18 each can be realized by, for example, executing a respective program by a processor. Alternatively, some or all of these units can be realized by hardware such as logic circuit. Or each of these units can be realized by a combination of a hardware device and a software program which controls the hardware device.

Next, the operation of the converting device 1, which has the above-described structure, will now be described.

In the case where medical image data of an old format, which were collected in the past and stored on a recording medium, are to be fetched into the image server 4, the media reading device 2 reads appropriate medical image data from the recording medium. The media reading device 2 sends the read medical image data to the converting device 1. The medical image data sent from the media reading device 2 are read by the SCSI interface unit 11 and then supplied to the format converting unit 14.

On the other hand, in the case where medical image data of an old format, which were created by the modality 3, are to be fetched into the image server 4, the needed medical image data are sent from the modality 3 to the converting device 1. The medical image data sent from the modality 3 are fetched in the LAN interface unit 12 and the old protocol processing unit 13 and then supplied to the format converting unit 14.

When the medical image data are supplied from the SCSI interface unit 11 or the old protocol process unit 13 thereto, the format converting unit 14 converts the medical image data from the old format into the DICOM format. It should be noted here that during the conversion, the data of each pixel are not changed at all. Therefore, when the medical image data contain additional data, the converted medical image data of the new format contain the original additional data as they are.

Figure 2:
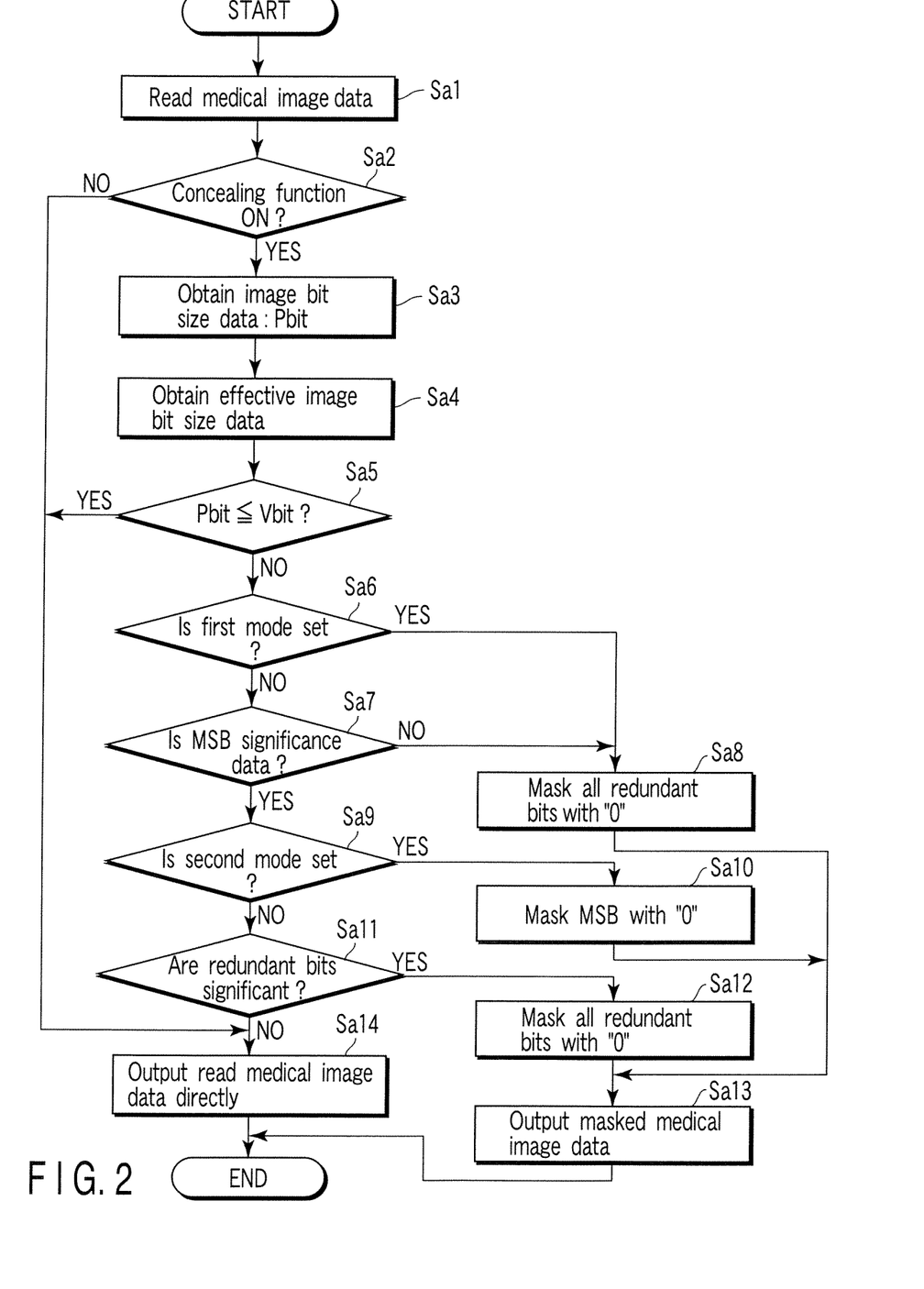
FIG. 2 is a flowchart that illustrates the processing procedure of a masking unit shown in FIG. 1.

The converted medical image data of the new format are supplied from the format converting unit 14 to the masking unit 17. Then, the masking unit 17 executes a process as illustrated in FIG. 2.

In step Sa1, the masking unit 17 reads the medical image data supplied from the format converting unit 14. The masking unit 17 temporarily holds the read medical image data.

In step Sa2, the masking unit 17 confirms whether the concealing function is on or not. The masking unit 17 presets ON/OFF of the concealing function based on the instruction entered by the user. When the concealing function is ON, the masking unit 17 moves on from step Sa2 to step Sa3. In step Sa3, the masking unit 17 obtains pixel bit size data contained in attached data to the medical image data, and substitutes the image bit size expressed by the pixel bit size data to a variable Pbit. It should be noted that the pixel bit size is the size of bit that is assigned to one pixel. Next, in step Sa4, the masking unit 17 obtains effective pixel bit size data contained from the attached data, and substitutes the effective image bit size expressed by the effective pixel bit size data to a variable Vbit. It should be noted that the effective pixel bit size is the size of bit of one pixel in actual data.

In step Sa5, the masking unit 17 confirms whether or not Vbit is smaller than Pbit. If Vbit is smaller than Pbit, only part of the bits for the pixel is used by the actual data, which indicates redundant bits are included. The redundant bits may possibly be additional data. Therefore, if Vbit is smaller than Pbit, the step advances from step Sa5 to step Sa6.

In step Sa6, the masking unit 17 confirms whether or not the first mode is set. It should be noted that the masking unit 17 presents one of the first to third modes based on the instruction made by the user. If the first mode is set, the masking unit 17 moves on from step Sa6 to step Sa8. If the first mode is not set, the masking unit 17 moves on from step Sa6 to step Sa7. In step Sa7, the masking unit 17 confirms whether or not the MSB (most significant bit) in the bit row for one pixel is significance data based on the attached data. The significance data are data indicating whether or not the bit row of redundant bits is effective additional data. If the MSB is not significance data, the masking unit 17 moves on from step Sa7 to step Sa8. In step Sa8, the masking unit 17 masks all the redundant bits with "0". After that, the masking unit 17 moves on to step Sa13.

Figure 3:
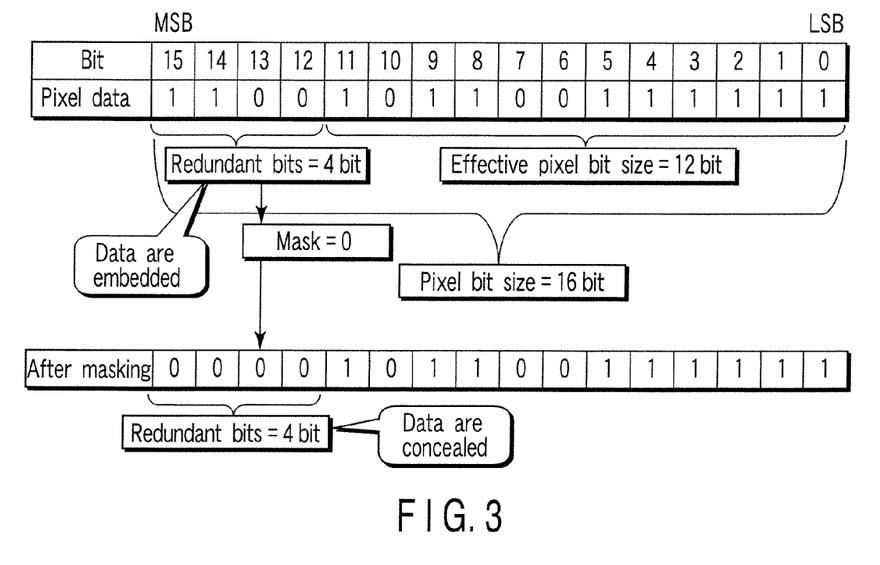
FIG. 3 is a diagram showing how the mask processing is carried out in step Sa8 shown in FIG. 2.

FIG. 3 is a diagram showing how the above-described mask process is carried out. In the example shown in FIG. 3, the pixel bit size is 16 bits and the effective pixel bit size is 12 bits. Thus, the upper 4 bits are redundant bits. The masking unit 17 masks all of the upper 4 bits with "0" as shown in FIG. 3. In this manner, when the additional data are embedded in the redundant bits, the additional data are invalidated. In other words, the personal data and the like, expressed by the addition data are concealed.

When it is confirmed that the MSB is significance data in step Sa7, the masking unit 17 moves on to step Sa9. In step Sa9, the masking unit 17 confirms whether or not the second mode is set. If the second mode is set, the masking unit 17 moves on from step Sa9 to step Sa10. In step Sa10, the masking unit 17 masks the MSB with "0" regardless of the state of the MSB. After that, the masking unit 17 moves on to step Sa13.

Figure 4:
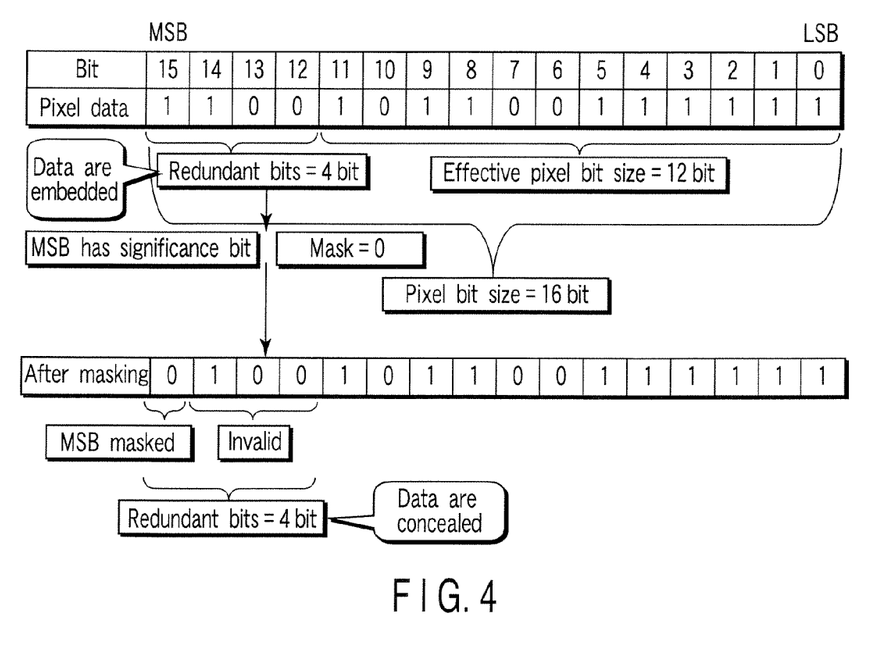
FIG. 4 is a diagram showing how the mask processing is carried out in step Sa10 shown in FIG. 2.

FIG. 4 is a diagram illustrating how the mask process is carried out in the above-described situation. The significance data, when "1", indicate that the bit row of the redundant bits are effective additional data. Therefore, when the MSB, that is, the significance data, are changed to "0" as shown in FIG. 4, the additional data embedded in the redundant bits are invalidated. In other words, the personal data and the like expressed by the additional data are concealed.

If the second mode is not set, namely, if the third mode is set, the masking unit 17 moves on from step Sa9 to step Sa11. In step Sa11, the masking unit 17 confirms whether or not the redundant bits are significant based on the significance data. If the redundant bits are significant, the masking unit 17 moves on from step Sa11 to step Sa12. In step Sa12, the masking unit 17 masks all the redundant bits with "0". After that, the masking unit 17 moves on to step Sa13.

Figure 5:
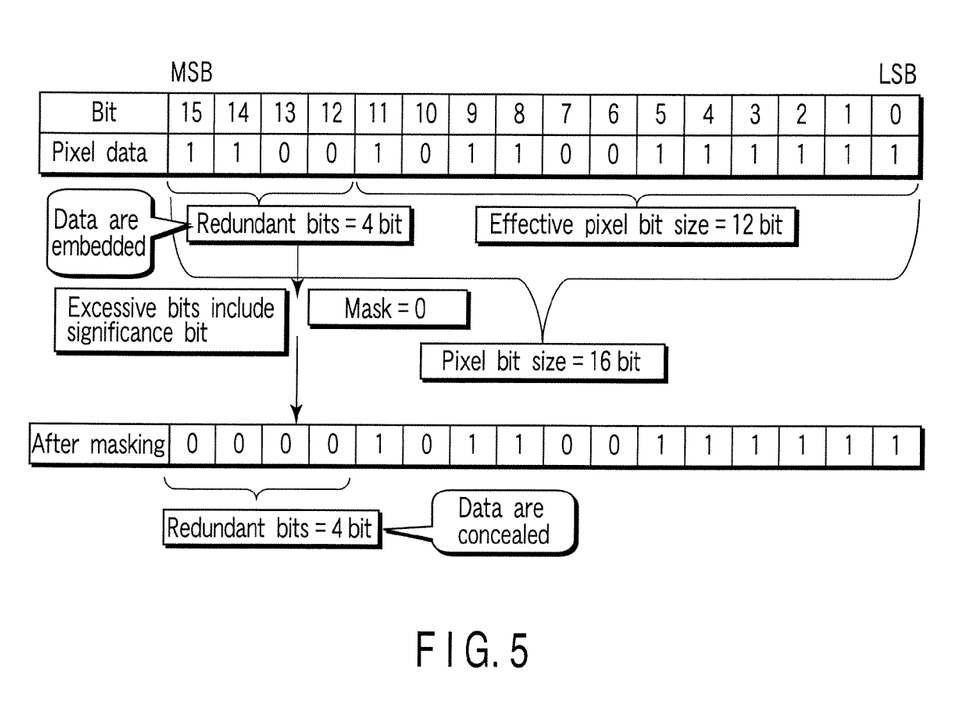
FIG. 5 is a diagram showing how the mask processing is carried out in step Sa12 shown in FIG. 2.

FIG. 5 is a diagram illustrating how the mask process is carried out in the above-described situation. Since the significance data is "1", all the upper 4 bits are masked with "0". In this manner, the additional data embedded in the redundant bits are invalidated. In other words, the personal data and the like expressed by the additional data are concealed.

Here, it should be noted that the objects to be processed by the masking unit 17 in steps Sa8, 10 and 12 are the data regarding pixels located within an object area designated in advance by the user. When the object area is designated as the "entire area", the masking unit 17 carries out the above-described mask process on the data of all the pixels in steps Sa8, 10 and 12. When a part of the medical image is designated as the object area, the masking unit 17 carries out the above-described mask process on the data of the pixels located within only the designated area in steps Sa8, 10 and 12. The masking unit 17 displays the medical image expressed by the medical image data and text image on the display unit 15 for the user to be able to designate an object area on the displayed image. When the object area is designated as "automatic", the masking unit 17 recognizes the text image expressed by the additional data by character pattern recognition, and identifies the area that contains a character row matching the pre-set conditions. Then, the masking unit 17 carries out the above-described mask process on the data of the pixels located within only the identified area in steps Sa8, 10 and 12. It should be noted here that the character row matching the conditions may be set as a character row including a keyword designated in advance by the user or that including a word phrase that can be assumed on the analogy of the keyword. Typical examples of the keyword are the "name", "age", "birth date", "ID", "height" and "weight" of the patient.

Figure 6:
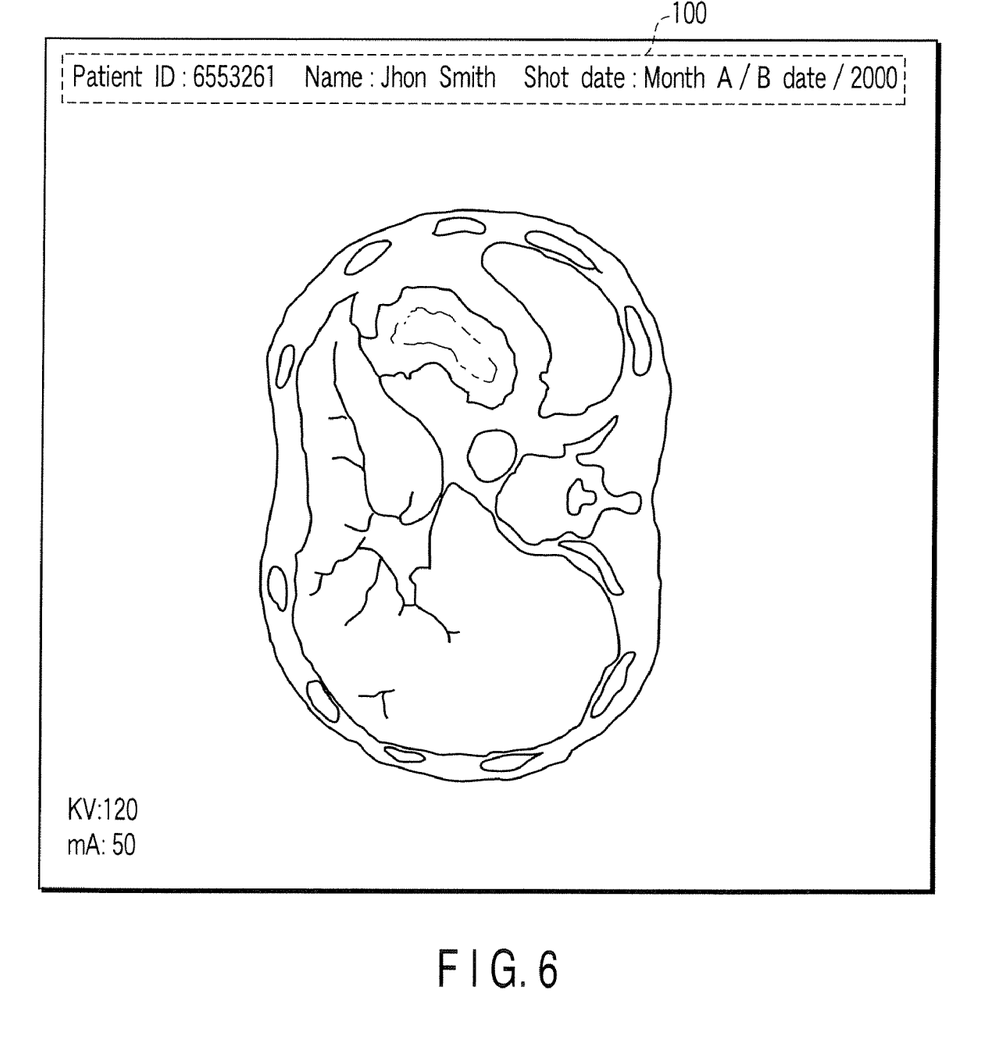
FIG. 6 is a diagram showing an example of the image expressed by medical image data before the mask process.
Figure 7:
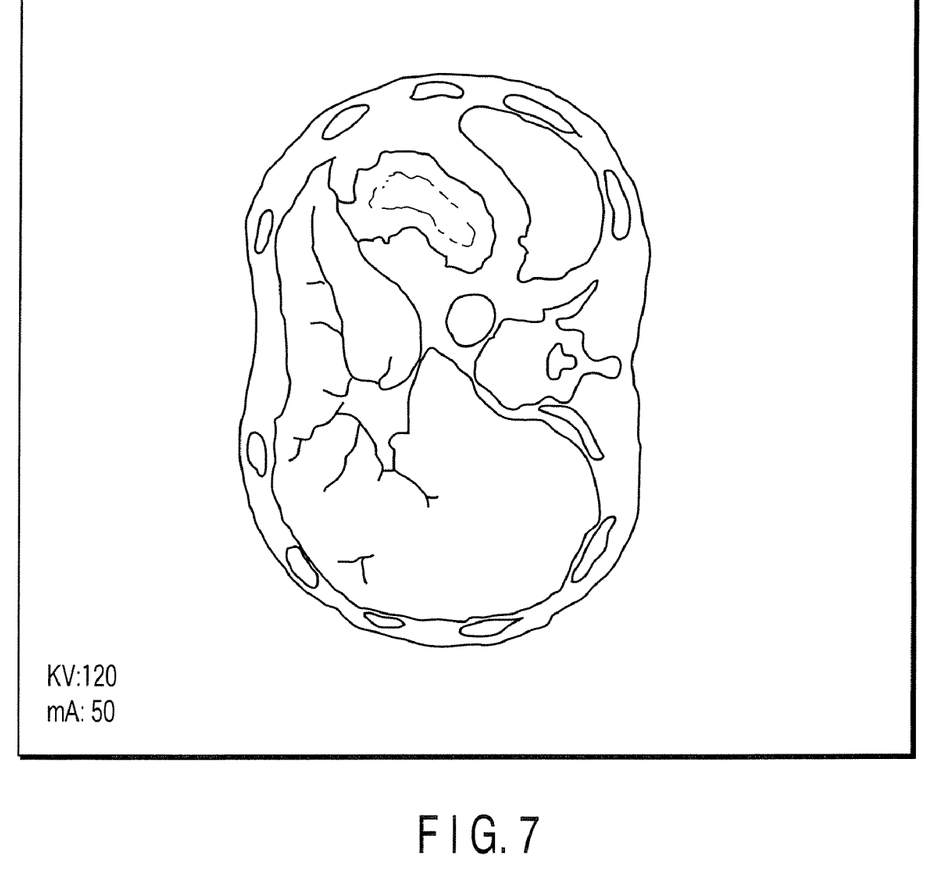
FIG. 7 is a diagram showing the first example of the image expressed by medical image data after the mask process.
Figure 8:
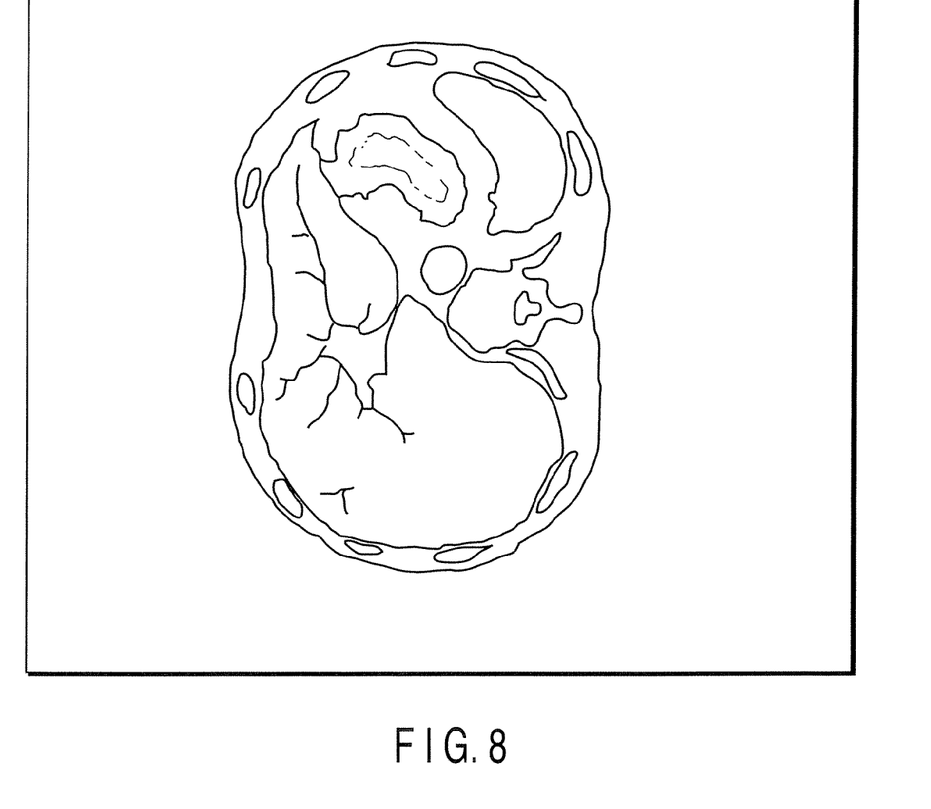
FIG. 8 is a diagram showing the second example of the image expressed by medical image data after the mask process.

Let us suppose here that medical image data expressing an image such as shown in FIG. 6 are an object to be processed. In FIG. 6, "patient ID: 6553261", "name: John Smith", "shot date: A month B date of year 2000", "kV: 120" and "mA: 50" are the characters expressed based on the additional data.

Figure 9:
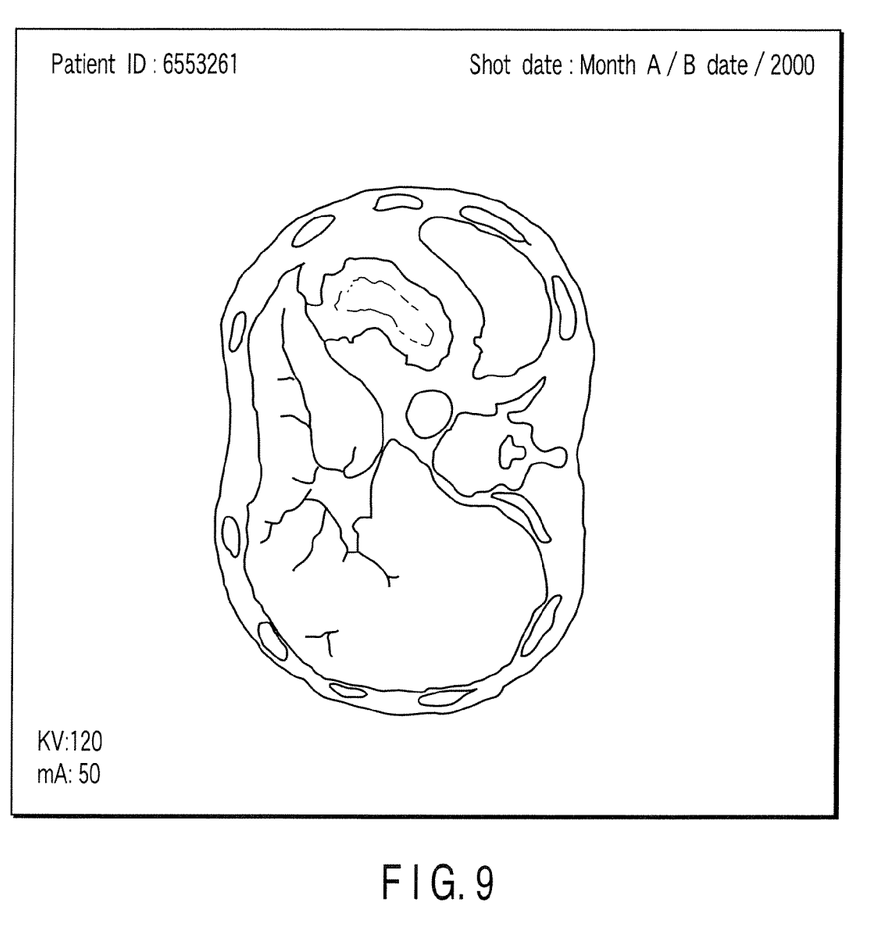
FIG. 9 is a diagram showing the third example of the image expressed by medical image data after the mask process.

Here, if an area 100 shown in FIG. 6 is designated as an object area, the characters in the area 100, that is, "patient ID: 6553261", "name: John Smith" and "shot date: A month B date of year 2000" are masked, whereas the characters, "kV: 120" and "mA: 50" are not masked. By contrast, the object area is designated as the "entire area", all of the characters, that is, "patient ID: 6553261", "name: John Smith", "shot date: A month B date Lof year 2000", "kV: 120" and "mA: 50" are masked. On the other hand, if the object area is designated as the "automatic" and only the "name" of the patient is designated as the keyword, the characters of only "name: John Smith" are masked as shown in FIG. 9.

In step Sa13, the masking unit 17 outputs the medical image data already subjected to the mask process in one of steps Sa8, 10 and 12 to the DICOM processing unit 18. Then, the masking unit 17 finishes the process illustrated in FIG. 2.

On the other hand, when it is confirmed in step Sa11 that the redundant bits are not significant, the masking unit 17 moves on to step Sa14. It should be noted that in the case where the concealing function is set to OFF or Vbit is not smaller than Pbit, that is, there is no redundant bits, the masking unit 17 moves on from step Sa2 or Sa5 to step Sa14. In step Sa14, the masking unit 17 outputs the medical image data read in step Sa1 directly to the DICOM processing unit 18. Then, the masking unit 17 finishes the process illustrated in FIG. 2.

The medical image data output from the masking unit 17 are transferred to the image server 4 by the DICOM processing unit 18 and the LAN interface unit 12.

As described above, according to this embodiment, if the concealing function is set to ON and the medical image data include redundant bits, the data of the redundant bits are invalidated. The invalidation is carried out in various methods depending on which one of the first to third modes is set. Therefore, the user can arbitrarily select a method for invalidating the data of redundant bits. In the first mode, all of the redundant bits are masked regardless of any conditions, the additional data can be completely concealed. In the second mode, only the MSB is masked, and therefore the number of bits to be masked can be significantly reduced as compared to the case of the first mode, thereby making it possible to shorten the processing time. In the third mode, all the redundant bits are masked, and therefore the additional data can be completely concealed. Further, according to the third mode, masking is carried out only when significant additional data are embedded in the redundant bits, and therefore the number of bits to be masked can be significantly reduced as compared to the case of the first mode, thereby making it possible to shorten the processing time. It should be noted that in the second or third mode, the additional data cannot be accurately invalidated when the MSB is not of significance data. However, according to this embodiment, when the MSB is not of significance data, all the redundant bits are masked regardless of any conditions even if the second or third mode is set. In this manner, the additional data can be accurately concealed.

This embodiment can be remodeled into various versions, which will now be described in the following.

That is, it is possible to apply only one or two of the three masking methods described above.

The masking process may be carried out before the format conversion.

It is possible that only the masking process is carried out without performing the format conversion.

In the case where medical image data in which additional data are embedded only in part of redundant bits are an object to be processed, it is possible that only the bits in which the additional data are embedded are masked in step Sa8 and step Sa12.

The format conversion may be carried out not only when the medical image data are saved in the image server 4, but also when the image data are output in various situations. For example, it is possible that the medical image data after subjected to the format conversion are transferred directly to the imager, and a film that expresses the image corresponding to the format-converted medical image data is formed in the imager. With this procedure, a film that conceals the additional data can be easily formed and such a version is used when films are used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A converting device that carries out data conversion on medical image data expressing a state of one pixel of a medical image using effective bits, which are part of a plurality of bits for one pixel and expressing information other than the medical image using redundant bits, which express a state of each pixel of a text image superimposed on the medical image, and which are different part from that of the effective bits, the converting device comprising:

a determining unit detects a character row expressing personal data by character pattern recognition of the text image expressed by the redundant bits, and determines a pixel in an area containing the character row as an object to be invalidated; and an invalidating unit that invalidates data included in the pixel data determined as the object to be invalidated and expressed by the redundant bits by changing at least one bit of part of the medical image data.

2. The converting device according to claim 1, wherein the invalidating unit masks the redundant data with particular data.

3. The converting device according to claim 2, wherein each of the plurality of bits for one pixel in the medical image data is an effective bit or a redundant bit, and the medical image data includes additional data indicating the number of bits for one pixel and the number of bits of the effective bits, and wherein the invalidating unit determines the number of bits of the redundant bits based on the number of bits for one pixel and the number of bits of the effective bits, expressed by the additional data, and masks the redundant bits with data having the same number of bits determined.

4. The converting device according to claim 1, wherein the medical image data include significance data indicating significance of the redundant bits, and the invalidating unit masks the significance data with data indicating insignificant information.

5. The converting device according to claim 1, wherein the medical image data include significance data indicating significance of the redundant bits, and the invalidating unit masks the redundant bits with particular data when the significance data indicate significant information.

6. The converting device according to claim 5, wherein the significance data is included in the redundant bits, and the invalidating unit masks all of the redundant data including the significance data with the particular data.

7. The converting device according to claim 1, further comprising a fetching unit that fetches the medical image data, wherein the invalidating unit changes a bit of part of the medical image data fetched by the fetching unit.

* * * * *